United States Patent [19]

Saltzgaber-Muller

[11] Patent Number: 4,831,125

[45] Date of Patent: May 16, 1989

[54] DNA PROBE FOR CORYNEBACTERIUM KUTSCHERI

[75] Inventor: Josephine Saltzgaber-Muller, N. Chelmsford, Mass.

[73] Assignee: E. I. Du Pont de Nemours and Company, Wilmington, Del.

[21] Appl. No.: 750,182

[22] Filed: Jul. 1, 1985

[51] Int. Cl.$^4$ .................. C07H 21/00; C12Q 1/68; C12N 15/00

[52] U.S. Cl. .................. 536/27; 935/78; 435/6; 435/803; 435/172.3; 435/252.33

[58] Field of Search .............. 435/6, 803, 172.3, 253; 935/78; 436/501, 811, 63; 536/27

[56] References Cited

U.S. PATENT DOCUMENTS

| | | | |
|---|---|---|---|
| 4,278,765 | 7/1981 | Debabov et al. | 435/172.3 |
| 4,358,535 | 11/1982 | Falkow et al. | 435/5 |
| 4,446,237 | 5/1984 | Berninger | 436/504 |
| 4,477,571 | 10/1984 | Chang et al. | 435/172.3 X |
| 4,563,419 | 1/1986 | Ranki et al. | 436/804 X |

OTHER PUBLICATIONS

Barksdale, Bacteriol. Rev., 34, (1970) pp. 414 & 378.
Wirth, D. F. et al., Proc. Natl. Acad. Sci., 79:6999–7003 (1982).
Chou, S. et al., New England Journal of Medicine, 308:921–924 (1983).
Spector, S. A. et al., J. Infectious Diseases, 150:121–126 (1984).
Saltzgaber-Muller, J. et al., J. Clin. Micro., vol. 24, 1986, pp. 759–763.
Danhaive, P. et al., Int. J. Syst. Bacterial, vol. 32, 1982, pp. 70–76.
Athwal, R. S. et al., Int. J. Syst. Bacteriol., vol. 34, 1984, pp. 371–375.
Chemical Abstracts, vol. 66, No. 3, issued Jan. 16, 1967, p. 903, Abst. No. 9452K, Caren, L. D. et al., "The Role of . . . Corynebacterium Kutscheri".
Biological Abstracts, vol. 77, No. 5, issued Mar. 1, 1984, Abst. No. 36184, Tsuchitani, M. et al., "Naturally Occurring . . . Cardiac Lesions".
Groman, N. et al., Infect. Immun., vol. 42, 1983, pp. 48–56.

Primary Examiner—Charles F. Warren
Assistant Examiner—Jeremy M. Jay

[57] ABSTRACT

A method for detecting *Corynebacterium kutscheri* in biological material using a hybridization probe is disclosed. Preferably, the biological material is from a laboratory animal. A novel *C. kutscheri* specific DNA probe prepared in a specified manner is also disclosed.

7 Claims, No Drawings

DNA PROBE FOR CORYNEBACTERIUM KUTSCHERI

FIELD OF THE INVENTION

This invention relates to a DNA probe for detecting pathogenic bacterium in biological materials.

BACKGROUND OF THE INVENTION

*Corynebacterium kutscheri* is a pathogen which produces pseudotuberculosis in laboratory animals. The infection commonly exists undetected in a putative latent form which becomes active when infected animals are subjected to resistance-lowering stress. Once *C. kutscheri* is introduced into a colony of laboratory animals, the pathogen is difficult to eradicate. The pathogenicity for the mouse and rat is well documented. Since infected animals cannot be used for experimentation, an effective method of rapidly evaluating laboratory animals for *C. kutscheri* infection would be extremely helpful.

The putative latent form of *C. kutscheri* infection is difficult to detect. Methods of detecting unapparent infections includes provocation testing with cortisone acetate, immunological testing, and serological testing by anamnesic response. Provocation tests are effective in detecting silent contamination, but result in propagation of infective agents. Diagnostic results are obtained in 7 to 10 days. Immunological tests are not completely effective because recently infected animals require 10 to 14 days to produce detectable amounts of antibody. Immunological tests also involve cross-reactivity problems.

Hybridization-probes are known in the field of molecular biology. U.S. Pat. No. 4,358,535, issued to Falkow on Nov. 9, 1982, discloses a process for detecting DNA sequences of pathogens of interest in raw clinical samples. Samples are placed onto a solid support and deposited microbes are treated to release DNA. The DNA is complexed onto the support and denatured. A labeled polynucleotide probe specific for a DNA sequence characteristic of a pathogen is contacted to the support under hybridization conditions. Hybridization of pathogenic DNA is detected by means of the probe label.

Wirth and Pratt, *Proc. Natl. Acad. Sci.*, 79: 6999 to 7003 (1982) disclose a method for detecting kinetoplast DNA (kDNA) of Leishmania species in cutaneous lesions. Blots are prepared by touching excised lesions on nitrocellulose filters. Species-related minicircles of kDNA are isolated from cultured Leishmania promastigotes and labeled radioisotopically. The nitrocellulose filter is hybridized with the labeled kDNA. Hybridization is detected on film.

U.S. Pat. No. 4,446,237, issued to Berninger on May 1, 1984, discloses a method for detecting viral DNA in acellular biological fluid. Solutions of denatured DNA isolated from acellular biological fluid are applied to a solid support. Viral DNA is denatured and labeled radioisotopically. The labeled DNA is contacted to the support under hybridization conditions. Hybridization of viral DNA is detected by means of the radioisotope label.

The following are representative of other typical DNA probe references. Chou and Merigan, *New England Journal of Medicine*, 308: 921 (1983) disclose the detection of cytomegalovirus DNA in clinical urine specimens after immobilization on nitrocellulose filters and hybridization with a radioactively labeled, cloned fragment of cytomegalovirus DNA. Spector et al., *J. Infectious Diseases*, 150: 121 (1984) disclose a diagnostic assay for the detection of human cytomegalovirus (HCMV) DNA in clinical specimens with $^{32}$P-labeled cloned fragments at HCMV DNA.

SUMMARY OF THE INVENTION

The present invention provides a method for detecting *Corynebacterium kutscheri* suspected to be contained in biological materials. The method comprises (a) contacting and treating the suspect biological material to immobilize any *C. kutscheri* DNA present in the biological material on a solid substrate in substantially single-stranded form, (b) contacting the immobilized single-stranded DNA with a labeled *C. kutscheri* specific DNA probe under hybridization conditions, and (c) detecting duplex formation on the solid substrate by means of the probe label.

This invention also provides a novel DNA probe for detecting *C. kutscheri* which is prepared by a specified process.

DETAILED DESCRIPTION OF THE INVENTION

The invention of a DNA probe specific to *C. kutscheri* required overcoming the known difficulty of breaking open the cell wall of Corynebacterium; the isolation of the entire DNA in substantially unbroken form from *C. kutscheri* and other nonpathogenic strains of Corynebacterium; and the identification from thousands of generated DNA fragments those capable of hybridizing with *C. kutscheri* DNA but not capable of hybridizing with the DNA from any of the 15 or so nonpathogenic strains of Corynebacterium.

As used herein, the expression "*C. kutscheri* specific DNA probe" means one or more fragments of DNA which are useful in detecting substantially unique sequences in the DNA of *C. kutscheri*. The selected probe must be capable of hybridizing with single-stranded *C. kutscheri* DNA but incapable of hybridizing with single-stranded DNA from nonpathogenic strains of Corynebacterium, i.e., must be specific to *C. kutscheri*. In addition, the probe must be incapable of cross-reacting with the DNA of the biological material.

Nineteen strains of Corynebacterium were used in the concentration of a *C. kutscheri* specific DNA probe. Four strains designated M1572-1, M2519, M1997-1 and the ATCC strain 15677 are *C. kutscheri;* eleven strains numbered CRL-1 through CRL-11 are nonpathogenic strains isolated from laboratory rats by Charles River Laboratories. In addition, four strains numbered 3703-1, 3922-1, 3967-1 and 3968-1 are nonpathogenic strains isolated from laboratory rats by E. I. Du Pont de Nemours and Company.

Homology studies were done to determine the overall relatedness of the DNA of nonpathogenic Corynebacterium to *C. kutscheri* DNA. While twelve of the nonpathogenic strains shared low homology with pathogenic DNA (<3.9%), three nonpathogenic strains (CRL-1, CRL-2 and CRL-5) exhibited a relatively high degree of homology (19.7, 24.6 and 60.3%, respectively). Thus, intact pathogenic DNA could not be used to probe biological materials for the presence of *C. kutscheri*. The isolation of a *C. kutscheri* specific DNA probe required the isolation and testing of different sized fragments of *C. kutscheri* genomic DNA. To demonstrate that a *C. kutscheri* specific probe is capable of detecting all pathogenic strains of Corynebacterium, homology studies were done on DNA isolated from 4 to 5 known pathogenic strains which revealed about 100% homology.

The results of the homology studies indicate that any strain of *C. kutscheri* is suitable for probe preparation. *C. kutscheri* strain M1572-1 has been deposited with the American Type Culture Collection (ATCC), Rockville, Md. and bear deposit accession number ATCC 53150. This deposit is available to the public upon the grant of a patent to the assignee. *C. kutscheri* strain ATCC 15677 is also available from the ATCC. In addition, *C. kutscheri* can be isolated from lesions present in infected animals by techniques known in the art. Nonpathogenic Corynebacterium are also available from the ATCC and can be isolated from laboratory animals and other sources by techniques known in the art.

In the method of the present invention, any restriction endonuclease capable of generating *C. kutscheri* specific probe is suitable for probe preparation. *C. kutscheri* specific digestion fragments are cloned into a vector capable of transforming bacteria. Bacteria are transformed with the vector containing the selected digestion fragments and cultivated. Transformed cells are harvested and the plasmids are isolated. The plasmids are digested with any restriction enzyme capable of removing the *C. kutscheri* fragments. Fragments specific to *C. kutscheri* are isolated and labeled to form probes of the present invention.

A variety of restriction endonucleases are suitable for probe preparation. A partial list of suitable restriction endonucleases includes Sau 3A, Mbo I, and EcoR1. These endonucleases were screened for use in the preparation of a preferred *C. kutscheri* specific probe. Preferably, the probe is prepared by digesting *C. kutscheri* DNA in substantially unbroken form with restriction endonuclease EcoR1 and resolving generated fragments according to their respective sizes, preferably by agarose gel electrophoresis. Blot hybridization, conducted according to a method similar to that of Southern, *J. Mol. Biol.*, 98: 500–517, (1975), incorporated herein by reference, is used to select digestion fragments capable of hybridizing with *C. kutscheri* DNA but incapable of hybridizing with nonpathogenic Cornyebacterium DNA and incapable of hybridizing with DNA of the selected biological material.

The resulting *C. kutscheri* specific digestion fragments are cloned into a vector capable of transforming bacteria to enable selection of individual fragments of *C. kutscheri* DNA for hybridization studies. The preferred vector is plasmid pBR322 or plasmid pBR325 and the preferred bacteria is *E. coli*. The construction and characterization of plasmid pBR322 is taught by Bolivar et al., *Gene,* 2: 95–113 (1977), which is incorporated herein by reference. Preferably, the *E. coli* is *E. coli* HB101 or *E. coli* RR1. Bacteria are transformed with the plasmids containing the selected digestion fragments and cultivated. Cloning and transformation are accomplished by techniques well known in the art. These techniques are described in many references including Maniatis et al., *Molecular Cloning, A Laboratory Manual,* Cold Spring Harbor Laboratory, (1982). Transformed cells are harvested and the plasmids are isolated. Techniques for isolating plasmids, like cesium chloride gradient centrifugation, are known in the art.

In order to avoid any cross-hybridization between the vector and bacterial DNA, fragments of *C. kutscheri* DNA are removed from the isolated plasmids, prior to testing their efficacy as probes. Any restriction enzyme capable of removing the cloned *C. kutscheri* DNA from the vector would be suitable. Restriction enzyme analysis determined that the restriction enzyme, HindIII, generated a good size range of fragments for testing as probes on a large scale basis. Digestion fragments are resolved according to their respective sizes, preferably by agarose gel electrophoresis. Southern Blot hybridization is again used to identify *C. kutscheri* specific digestion fragments. Preferably, the probe is at least one of three fragments which are about 1.6 kb, 1.7 kb, and 1.8 kb in size and which result from the foregoing procedure.

*E. coli* HB101, transformed with plasmid pBR322 containing the three preferred probe fragments, mentioned above, have been deposited with the American Type Culture Collection (ATCC), Rockville, Md. Plasmids containing the probe fragments which are about 1.6 kb, 1.7 kb, and 1.8 kb in size bear deposit accession numbers ATCC 53153, 53151, and 53152, respectively. These deposits are available to the public upon the grant of a patent to the assignee. However, it should be understood that the availability of a deposit does not constitute a license to practice the subject invention in derogation of patent rights granted by government action. The preferred probe fragments can be prepared from the deposited plasmids with restriction enzyme HindIII. These deposits represent a preferred embodiment and do not limit the scope of the present invention.

The selected specific DNA fragment or fragments are labeled to provide the probe of the invention. Any label capable of binding to the selected DNA fragment or fragments and identifying duplex formation on the solid substrate would be suitable. Labeling agents which can be used include radioisotopes, chemiluminescers, fluorescers, phosphorescers, protein coupled nucleotides, biotin coupled nucleotides, zymogen coupled nucleotides, or heavy metal coupled nucleotides. Preferably, the labeling agent is a radioisotope. Suitable radioactive labels include $^{32}P$, $^{3}H$, $^{14}C$, or the like. Most preferably, the probe is labeled with $^{32}P$ using nick translation. Techniques for labeling the selected DNA fragment or fragments with the selected labeling agent are known in the art. A technique for labeling DNA with $^{32}P$ using nick translation is described by Rigby, *J. Mol. Biol.* 113: 237–251 (1977).

In the method of the present invention, the presence of *C. kutscheri* in biological material is detected. Any biological material suspected to contain *C. kutscheri* is suitable for probe evaluation in the method of the invention. The selected *C. kutscheri* specific probe should be incapable of hybridizing with DNA of the biological material. Preferably, the biological material is from a laboratory animal, most preferably a mouse or a rat. Suitable biological materials include fecal pellets, nasal swab, tongue and mouth wash, and tissue, but tissue is preferred. Preferably, the tissue is selected from the group comprising liver, lung, kidney, bone marrow, cervical lymph node, mandibular lymph node, ileum, nasal pharynx and cecum. Most preferably, the tissue is liver tissue.

In the method of the invention, touch blots are prepared from the biological material on a solid substrate. Preferably, blots are prepared according to a method similar to that of Wirth and Pratt, *PNAS,* 79: 6999–7003 (1982). The biological material is contacted with a solid substrate for sufficient time to immobilize any *C. kut-* scheri present in the material on the solid substrate. Timing is not critical. Preferably, the biological material is touched to the substrate for from about 30 to about 60 seconds. Dried blots can be stored in clean envelopes until hybridization is conducted. The solid substrate is then treated to lyse the C. kutscheri deposited from the biological material and affix the released DNA in substantially single-stranded form. Alternatively, the biological material is treated to extract and denature C. kutscheri DNA present in the material. The resulting preparation containing the denatured DNA is then contacted with the solid substrate. The resulting blots are allowed to air dry.

Solid substrates capable of fixing the C. kutscheri and the released DNA, and preserving the blots without degradation are suitable for use in the method of the present invention. Preferred solid substrates include nitrocellulose, nylon microprous membrane, and charged microporous membrane. The latter two preferred substrates are provided commercially by E. I. du Pont de Numerous and Company, Wilmington, Del., under the trademarks Gene Screen and Gene Screen Plus. Most preferably, the solid substrate is nylon microporous membrane. Preferably, blots prepared in nitrocellulose or nylon microporous membrane are baked at about 80° C. for about 1–2 hours before hybridization is conducted.

The C. kutscheri DNA on the touch blot must be available for hybridization. The difficulty associated with breaking open Corynebacterium cells and extracting released DNA in substantially single-stranded form is known. In the present method, treatments capable of extracting Corynebacterium DNA in substantially single-stranded form are suitable. Preferably, lysozyme and sodium hydroxide treatments are used to lyse C. kutscheri and denature the released DNA. In one embodiment, touch blots prepared on nitrocellulose are dried at ambient temperature and washed sequentially in 0.2M NaOH/1% SDS and 1M Tris Cl pH 8.0, each for 30 minutes at ambient temperature. The blots are then subjected to lysozyme digestion (1 mg/mL in 10 mM EDTA pH 8.0) for 30 minutes at ambient temperature. Touch blots prepared on changed nylon microporous membranes can be treated sequentially with 0.5M NaOH/1.5M NaCl for 30 minutes at ambient temperature and twice with 3M Tris Cl pH 8.0 for 30 minutes at ambient temperature to extract C. kutscheri DNA in substantially single-stranded form.

In the method of the invention, single-stranded DNA affixed to the solid substrate is contacted with a labeled C. kutscheri specific DNA probe under hybridization conditions. The blot containing the substantially denatured DNA from the suspect biological material is incubated in prehybridization solution. Preferably, the blot is incubated in a prehybridization solution at about 60° C. for at least about 2 to 6 hours. Labeled C. kutscheri specific DNA probe in a hybridization solution is then added to the prehybridization solution containing the blot. Suitable prehybridization and hybridization solutions are known in the art. The probe is incubated with the blot for sufficient time to allow the probe to hybridize with homologous DNA sequences immobilized on the blot. Preferably, the probe is incubated with the blot for about 16 to 24 hours at about 60°–70° C., most preferably 68° C. The resulting blots are washed to remove nonspecifically bound probe.

Duplex formation between the labeled C. kutscheri specific DNA probe and homologous DNA sequences immobilized on the solid substrate, is detected by means of the DNA probe label. Any method capable of detecting the selected probe label is suitable for detecting duplex formation. If a radioisotope label is being used it is preferably detected on X-ray film. Detection of duplex formation on the solid substrate indicates the presence of C. kutscheri in the biological material.

The invention is further described by the following examples; however, the scope of the invention is not to be limited thereby. In the Examples, all percentages are by weight, parts are by volume and degrees Celsius, unless otherwise stated. Homology studies were done substantially according to the following procedure.

Procedure for DNA Homology Studies

Homology studies were conducted with DNA from the 19 strain of Corynebacterium mentioned earlier herein and rat liver DNA according to a procedure similar to that of Danhaive et al., Int. J. Syst. Bacteriol., 32: 70–76 (1982). Unlabeled DNA (10 µg) in 0.9M NaCl/0.09M sodium citrate buffer (pH 7.6) was denatured by heating at 100° for five minutes and quick cooling on ice. The resulting denatured DNA was filtered through nitrocellulose filters (0.45 µm pore size, Schleicher and Schuell BA85). The filters were washed extensively with the same buffer, dried overnight at ambient temperature and baked for two hours at 80°. The baked filters were placed in a prehybridization solution of 0.45M NaCl/0.45M Na citrate buffer (pH 7.6) containing 0.02% wt/vol each of ficoll, polyvinyl pyrrolidone and bovine serum albumin at 68° for 2 hours, with replacement of the solution with fresh solution after one hour. Pathogenic strain M1572-1 DNA was labeled with $^{32}P$ according to a method similar to that of Rigby et al., J. Mol. Biol., 113: 237–251 (1977). For hybridization, 20 ng of the denatured radiolabeled DNA ($1.66 \times 10^5$ cpm) were added to each filter in 1.0 mL of the prehybridization solution. The filters were incubated at 68° for 16–18 hours, washed on both sides with 50 mL of 3 mM Tris Cl (pH 9.35), air dried and counted in a scintillation counter. Isologous hybridization figures were between 12% to 15% of input which was taken as 100%. Each assay was done in triplicate. The results of the homology studies are presented in Table I.

TABLE I

Hybridization of C. kutscheri M1572-1 DNA With Corynebacterium and Rat Liver DNA

| DNA Assayed | % Hybridization* with M1572-1 DNA |
|---|---|
| Non-Pathogens | |
| CRL-1 | 19.7 |
| CRL-2 | 24.6 |
| CRL-3 | 2.6 |
| CRL-4 | 3.5 |
| CRL-5 | 60.3 |
| CRL-6 | 1.0 |
| CRL-7 | 0.7 |
| CRL-8 | 2.1 |
| CRL-9 | 0.9 |
| CRL-10 | 3.9 |
| CRL-11 | 1.2 |
| 3922-1 | 0.3 |
| 3677-1 | 1.5 |
| 3968-1 | 1.4 |
| 3703-1 | 1.0 |
| Pathogens | |
| M1997-1 | 109.0 |
| M2519-1 | 117.0 |
| ATCC15677 | 84.5 |
| M1572-1 | (100) |

TABLE I-continued

**Hybridization of *C. kutscheri* M1572-1 DNA With Corynebacterium and Rat Liver DNA**

| DNA Assayed | % Hybridization* with M1572-1 DNA |
|---|---|
| RAT LIVER | 0.53 |

*Hybridization is expressed as a percentage of the isologous annealing value taken as 100.

EXAMPLE 1

Construction of *C. kutscheri* Specific DNA Probe

Example 1 shows the construction of a *C. kutscheri* specific DNA probe. The probe was constructed by a procedure which includes (1) isolting Corynebacterium and rat liver DNA, (2) isolating EcoR1 digestion fragments of *C. kutscheri* DNA, (3) selecting *C. kutscheri* specific EcoR1 digestion fragments, (4) transforming *E. coli* RR1 with plasmid pBR322 containing selected EcoR1 digestion fragments, (5) isolating cloned fragments from plasmid pBR322 and (6) selecting isolated cloned fragments suitable as probes.

(1) Isolation of Corynebacterium and Rat Liver DNA

The DNA from the 19 strains of Corynebacterium mentioned earlier herein was isolated by a modified procedure of Danhaive et al., *Int. J. Syst. Bacteriol.*, 32: 70–76 (1982). The Corynebacterium strains were grown in trypticase soy broth at 35° to late logarithmic stage of growth and harvested by centrifugation. The harvested cells were frozen (dry ice-ethanol bath) and thawed (50° water bath) three times and treated with lysozyme (1 mg/mL) for 1–2 hours at 50°. Pronase and sodium dodecyl sulfate (SDS) were added to the resulting mixture to a final concentration of 1 mg/mL and 1%, respectively. The mixture containing pronase and SDS was incubated for 1 hour at 37°. DNA was extracted from the resulting lysate with phenol at pH 7.6 and then with chloroform: isoamyl alcohol (24:1). After digestion with pre-treated pancreatic RNase (100 μg/mL, 2 hours at 37°) and re-extraction as above, the DNA was precipitated with ethanol. Purity of the isolated DNA was determined by UV spectrophotometry. Optical densities were determined in a recording spectrophotometer at 230, 260 and 280 nm. DNA having 260/280 and 260/230 optical density ratios of 2.0 or greater was used in hybridization experiments.

In addition, rat liver DNA was isolated according to a method similar to that of Blin and Strafford, *Nucl. Acids Res.*, 3: 2303–2308 (1976), which is incorporated herein by reference.

(2) Isolation of EcoR1 Digestion Fragments of *C. kutscheri* DNA

The DNA of strain M1572-1 was digested to completion with restriction enzyme EcoR1 (5U/μg; 2 hours at 37°) in a buffer containing 50 mM NaCl, 100 mM Tris HCl (pH 7.5), 5 mM $MgCl_2$ and 100 μg/mL bovine serum albumin. The resulting digest containing fragments ranging from about 300 to about 9500 base pairs was applied to a preparative 0.8% agarose gel (Bull's Eye Unit SE2020, Hoefer Scientific Company). During electrophoresis at 0.3A in Tris acetate buffer (4 mM Tris acetate, 2 mM EDTA), fractions of approximately 7 mL were collected over a period of 48 hours. The size of the fragments in each fraction was determined on horizontal agarose slab gels with ethidium bromide staining. Fractions were subsequently combined into six pools according to the following size ranges of fragments:

I—less than 300 to 1600 base pairs;
II—2200 to 3400 base pairs;
III—3500 to 4800 base pairs;
IV—5000 to 5500 base pairs;
V—7000 to 7500 base pairs;
VI—greater than 9500 base pairs.

The DNAs of each pool were obtained by ethanol precipitation.

(3) Selection of *C. kutscheri* Specific EcoR1 Digestion Fragments

The DNA of each strain of Corynebacterium was subjected to EcoR1 digestion as above. The generated fragments were fractionated on a 0.8% agarose slab gel. The DNA was denatured by sequential treatment of the gels with 0.5M NaOH/1.5M NaCl for 60 minutes and twice with 0.5M Tris Cl (pH 6.8)/3M NaCl for 45 minutes at ambient temperature. The DNA was transferred to nitrocellulose filters (BA85 Schleicher and Schuell) by the method of Southern, *J. Molecular Biol.*, 98: 500–517 (1975). The filters were dried in a vacuum at 80° for 2 hours and treated with a prehybridization solution (PS) containing 1×–10× Denhardt's buffer (Denhardt, *Biochem. Biophys. Res. Commun.*, 23: 641–646 (1966)), 1×SSC, 0.1% SDS and 100 μg/mL denatured Salmon sperm DNA for 2 hours at 68°, replacing the solution with fresh PS solution after 1 hour.

Pools II, III, IV, and V were radiolabeled with an $\alpha$-$^{32}$PdCTP by a method similar to that of Rigby et al., *J. Molecular Biol.*, 113: 237–251 (1977). Unincorporated radioactivity was removed either on a Sephadex-50 gel filtration column or, as in most cases, on a column containing a Teflon® nucleic acid purification cartridge, available commercially from E. I. Du Pont de Nemours and Company under the trade name NENSORB, which had been prewashed twice with 2.0 mL of methanol and three times with 1.0 mL of 1M Tris Cl, 1 mM EDTA, 10 mM triethylamine (pH 7.7). 500 μl of the latter buffer were added to the sample for loading onto the column. Non-reactive nucleotides were removed with buffer and the DNA was eluted with three 0.5 mL volumes of 20% ethanol.

Hybridization of the filters containing the Corynebacterium DNA, described above, was conducted in the PS solution, described above, containing 0.5–1.0×$10^6$ cpm/mL$^{32}$P of the labeled DNA from Pools II, III, IV and V according to a method similar to that described for DNA homology studies for 16 hours at 68°. The resulting filters were washed sequentially as follows: (1) 10 minutes at ambient temperature in 2×SSC, 0.5% SDS; (2) 20–30 minutes at ambient temperature in 1×SSC, 0.5% SDS; (3) 30 minutes at 42° in 0.5×SSC, 0.5% SDS; and (4) 30–45 minutes twice at 68° in 0.5×SSC, 0.5% SDS. The filters were air dried and exposed to X-ray film at −70° using an intensifying screen, available commercially from Du Pont under the registered trademark Cronex®. Pools II, IV, and V cross-hybridized extensively with at least 3 of the digested nonpathogenic strains (CRL-1, CRL-2, CRL-5). Pool III (size range 3500–4800 base pair fragments) showed only minor reaction with nonpathogenic DNAs. The fragments of Pool III were selected as potential probes.

(4) Transformation of E. coli RR1 with Plasmids Containing Selected EcoR1 Digested Fragments Plasmid pBR322 was cleaved with EcoR1 and treated with calf alkaline phosphatase (0.5 U/pmole 5'ends) in 10 mM glycine KOH (pH 9.0), 7 mM MgCl$_2$, 1 mM ZnCl$_2$ for 30 minutes at 37° and then heated for 20 minutes at 65°. The resulting vectors were ethanol precipitated. The fragments of pool III were ligated into the vector at a 2:2.24 molar ratio (insert:vector) in buffer containing 6 mM Tris Cl pH 8.0, 6 mM MgCl$_2$, 50 mM NaCl, 1 mM ATP, 10 mM dithiothreitol, 200 μg/mL bovine serum albumin, 1 mM spermidine and 10 U/ug T4 DNA ligase for 16 hours at 20°. The ligated material was used to transform E. coli RR1 cells according to a method similar to that of Bolivar et al., Gene, 2: 95-13 (1977). Randomly selected ampicillin resistant clones were examined for plasmid size by the method of Birnboim and Doly, Nucl. Acids Res., 7: 1513-1523 (1979), which is incorporated herein by reference. Four of the transformants contained plasmids of 12.45 kb, 13.3 kb, 9.56 kb, and 10.15 kb. These plasmids, designated pJSM2, pJSM3, pJSM6 and pJSM9, were selected for hybridization experiments.

(5) Isolation of Cloned Fragments from Plasmid pBR 322

Large-scale isolation of plasmids pJSM2, pJSM3, pJSM6 and pJSM9 was performed by a modified procedure of Bachavarov and Ivanoff, Prep. Biochem., 13: 161-166 (1983). Cells were grown and amplified with chloramphenicol (170 μg/mL) for 12-18 hours and harvested by centrifugation. The resulting cell pellets were suspended in cold 50 mM Tris Cl pH 8.0, 10 mM EDTA, 14% sucrose and incubated with lysozyme (1.0 mg/mL) for 30 minutes on ice. The resulting cell suspension was mixed with an equal volume of freshly prepared 0.2 m NaOH/1% SDS and gently shaken at 0°-4° for 5 minutes. An equal volume of 3M Na acetate pH 5.0 was added to the resulting mixture for continued incubation at 0°-4° for 30 minutes. The final mixture was centrifuged and the resulting supernatant was filtered through a quick filtration material for gelatinous grindates available commercially from Calbiochem-Behring Co. under the trade name Mira Cloth. After pancreatic RNase treatment (37° for 30 minutes), the filtered supernatant was brought to 0.2M NaCl. Isolation of the plasmid DNA was accomplished by extracting with an equal volume of chloroform:isoamyl (24:1) and precipitation with ethanol. Further purification of the plasmid DNA was by cesium chloride gradient centrifugation according to a procedure similar to that described in Maniatis et al., Molecular Cloning, A Laboratory Manual, Cold Spring Harbor Laboratory, 93-94 (1982).

The plasmids were digested with HindIII (2-3 U/μg, 2 hours at 37°) in 50 mM Tris (pH 8.0), 10 mM MgCl$_2$, 100 μg/mL bovine serum albumin and the resulting digestion fragments were resolved on 0.8% agarose horizontal gels by electrophoresis. The digest yielded the following size fragments (in kilobases); pJSM2—5.2, 3.4, 1.8, 1.1 and 0.95; pJSM3—4.5, 4.3, 1.6, 1.45 (doublet); pJSM6—6.9, 1.7, 0.96; pJSM9—9.0, 1.15. Fragments separated electrophoretically were excised in gel strips and purified by electroelution and DE52 column chromatography according to a procedure similar to that of Maniatis et al., 164-167 (1982) or by glass head extraction according to a procedure similar to that of Vogelstein and Gillespie, PNAS, 76: 615-619 (1979). Nine fragments of 1.8, 1.1, 0.95, 4.5, 1.6, 1.45, 1.7, 0.96 and 1.15 kilobases were selected as potential probes.

(6) Selection of C. kutscheri Specific HindIII Digestion Fragment

The nine isolated M1572-1 HindIII digestion fragments were radiolabeled with $^{32}$P according to a method similar to that of Rigby et al., J. Molecular Biol., 113: 237-251 (1977). The labeled fragments were tested as probes in Southern blots. The EcoR1 digestion fragments of the 19 strains of Corynebacterium were electrophoretically resolved on a 0.8% agarose gels and transferred on nitrocellulose filters, nylon microporous membranes, and charged nylon microporous membranes. The latter two membranes require somewhat different treatment in hybridization experiments from that used for nitrocellulose. The agarose gels containing the EcoR1 digestion fragment were treated sequentially with 0.2N-0.4N NaOH/0.6M NaCl for 30 minutes at ambient temperature and 0.5M Tris Cl pH 7.6/1.5M NaCl for 30 minutes at ambient temperature. The fragments were transferred in 0.025M Na$_2$ HPO$_4$/NaH$_2$ PO$_4$ (pH 6.5) or 1-10×SSC buffer. Following transfer, the membranes were briefly rinsed in the transfer buffer and air dried at ambient temperature. The nylon microporous membrane requires baking at 65°-80° for 2-4 hours. Charged nylon microporous membranes do not require baking. Prehybridization buffer consisted of 10×Denhardt's solution, 1M NaCl, 0.1% sodium pyrophosphate, 1% SDS, 10% dextran sulfate, and 100 μg/mL denatured salmon sperm DNA. The membranes were incubated in prehybridization buffer for 2 to 6 hours at 60°-65° in sealed plastic bags. The radiolabeled digestion fragments (0.5-1×10$^6$ cpm/mL) were added to the bag solution containing the membrane in prehybridization solution. Hybridization was carried out for 16-20 hours at 65°-68°. The filters were sequentially washed twice in 2×SSC for 5-10 minutes at ambient temperature, twice in 2×SSC/1% SDS at 65°-68° for 30 minutes, and twice in 0.1×SSC for 30 minutes at ambient temperature. The washed membranes were air dried and exposed to X-ray film at −70° using an intensifying screen, similar to that described in Example 1.

Hybridization assays were performed on EcoR1 digestion fragments of selected strains of Corynebacterium. The results obtained in a number of hybridization experiments are summarized in Table II. The assays always included CRL-1, CRL-2, and CRL-5 due to their extensive homology with the pathogen. The following fragments were immediately rejected as potential probe fragments—the 1.1 kb and 0.95 kb fragments from pJSM2; the 4.5 and 1.45 kb fragments from pJSM3; and the 0.96 kb fragment from pJSM6; and the 1.15 kb fragment from pJSM9. The 1.8 kb fragment from pJSM2 and the 1.6 kb fragment from pJSM3 showed cross-reactivity only with pathogenic DNAs. The C. kutscheri specificity of these fragments was confirmed in further assays which included all 15 nonpathogenic EcoR1 digested DNAs. The 1.7 kb fragment from the pJSM6 HindIII digest was regarded as a viable probe because the fragment did not cross-hybridize with CRL-1, CRL-2, or CRL-5 digested DNAs. The three selected fragments of 1.6, 1.7 and 1.8 kb demonstrated strong cross-reactivity in hybridization assays.

TABLE II

Hybridization of Isolated *C. kutscheri* DNA Fragments With Non-Pathogenic Corynebacteria DNAs

| DNAs | pJSM2 fragments (kilobases) | | | pJSM3 fragments (kilobases) | | | pJSM6 fragments (kilobases) | | pJSM9 fragments (kilobases) |
|---|---|---|---|---|---|---|---|---|---|
| | 1.8 | 1.1 | 0.95 | 4.5 | 1.6 | 1.45 | 1.7 | 0.96 | 1.15 |
| CRL-1 | − | + | + | + | − | + | − | + | + |
| CRL-2 | − | + | + | + | − | + | − | + | + |
| CRL-3 | − | | | − | | | | | |
| CRL-4 | − | | | − | | | | | |
| CRL-5 | − | + | + | + | − | + | − | + | + |
| CRL-6 | − | | | + | − | + | | + | |
| CRL-7 | − | | | − | | | | | |
| CRL-8 | − | | | + | − | + | | + | |
| CRL-9 | − | + | + | + | − | + | − | + | |
| CRL-10 | − | | | + | − | + | | + | |
| CRL-11 | − | | | − | | | | | |
| 3922-1 | − | | | | | | | | |
| 3677-1 | | | | + | − | + | | + | |
| 3968-1 | − | | | − | | | | | |
| M1592-1 | + | + | + | + | + | + | + | + | + |
| M2519-1 | + | + | + | + | + | + | + | + | + |
| M1997-1 | | | | + | | | | | |

− = no hybridization
+ = hybridization
Blank = not determined

EXAMPLE 2

Detection of *C. kutscheri* in Tissue Touch Blots

Example 2 shows the detection of *C. kutscheri* in touch blots by hybridization with the DNA probe of Example 1. Touch blots were prepared on charged nylon microporous membranes with tissues from laboratory rats infected with *C. kutscheri* and non-infected animals according to a method similar to that of Wirth and Pratt, *PNAS*, 79: 6999–7003 (1982). Infected animals were sacrificed 1 week, 6 weeks, and 9 weeks after being injected with *C. kutscheri*. Blots were prepared from lung, kidney, liver, cervical lymph, nodes, nasal pharynx, cecum, tongue, mouth wash, ileum, oral swab, and mandibular lymph nodes. Tissues were removed from the animals, cut into 2–3 mm pieces, and touched to a charged nylon microporous membrane for 30 seconds to one minute. Mouth washes and oral swabs were also touched to a charged nylon microporous membrane for the same period of time. Blots of each type of biological material were not prepared for each animal.

The resulting membranes were treated sequentially with 0.5M NaOH/1.5M NaCl for 30 minutes at ambient temperature and twice with 3M Tris Cl pH 8.0 for 30 minutes at ambient temperature, air dried and baked for 1 hour at 80°. Blots were also prepared from *C. kutscheri* cells and rat liver DNA as controls. Prehybridization, radiolabeling of probe fragments, and hybridization were conducted according to a method similar to that described in Example 1. Three radiolabeled fragments (1.6 kb, 1.7 kb, and 1.8 kb) prepared according to a method similar to that of Example 1 were used as probes for different blots. The results are shown in Table III. The specified probes did hybridize with blots prepared from *C. kutscheri* cells but did not hybridize with blots prepared from rat liver DNA.

Hybridization was detected with each of the probe fragments on almost every blot prepared from animals infected with *C. kutscheri*. Every blot prepared from animals infected for 1 week and 6 weeks hybridized with the probe fragments. Blots prepared from non-infected animals showed no hybridization.

TABLE III

Hybridization of Probe Fragments with Tissue Touch Blots

| Animal | Description | Probe Fragment | Blot Hybridized | Results |
|---|---|---|---|---|
| 1 | Infected for 1 week | 1.8 kb | liver | + |
| | | | cervical lymph nodes | + |
| 2 | Infected for 1 week | 1.7 kb | liver | + |
| | | | cervical lymph nodes | + |
| 3 | Infected for 1 week | 1.8 kb | liver | + |
| | | | kidney | + |
| | | | lung | + |
| | | | nasal pharynx | + |
| | | | cervical lymph nodes | + |
| | | | cecum | + |
| 4 | Infected for 1 week | 1.6 kb | liver | + |
| | | | kidney | + |
| | | | lung | + |
| | | | nasal pharynx | + |
| | | | cervical lymph nodes | + |
| | | | cecum | + |
| 5 | Infected for 1 week | 1.7 kb | liver | + |
| | | | kidney | + |
| | | | lung | + |
| | | | nasal pharynx | + |
| | | | cervical lymph nodes | + |
| | | | cecum | + |
| 6 | Infected for 1 week | 1.8 kb | liver | + |
| | | | kidney | + |
| 7 | Infected for 1 week | 1.7 kb | liver | + |
| | | | lung | + |
| | | | kidney | + |
| 8 | Infected for 6 weeks | 1.8 kb | lung | + |
| | | | kidney | + |
| 9 | Infected for 6 weeks | 1.6 kb | kidney | + |
| 10 | Infected for 6 weeks | 1.7 kb | lung | + |
| | | | kidney | + |
| | | | cervical lymph nodes | + |
| | | | mouth wash | + |
| | | | liver | + |
| 11 | Infected for 9 weeks | 1.8 kb | liver | + |

TABLE III-continued

Hybridization of Probe Fragments with Tissue Touch Blots

| Animal | Description | Probe Fragment | Blot Hybridized | Results |
|---|---|---|---|---|
| 12 | Infected for 9 weeks | 1.6 kb | cervical lymph nodes | − |
|  |  |  | tongue | − |
|  |  |  | mouth wash | − |
|  |  |  | liver | + |
|  |  |  | cervical lymph nodes | + |
|  |  |  | tongue | + |
| 13 | Not infected | 1.7 kb | mouth wash | − |
|  |  |  | lung | − |
|  |  |  | liver | − |
|  |  |  | kidney | − |
|  |  |  | ileum | − |
|  |  |  | oral swab | − |
|  |  |  | mandibular lymph nodes | − |
| 14 | Not infected | 1.8 kb | lung | − |
|  |  |  | liver | − |
|  |  |  | kidney | − |
|  |  |  | ileum | − |
|  |  |  | oral swab | − |
|  |  |  | mandibular lymph nodes | − |

Notes:
+ = hybridization detected
− = no hybridization detected

What is claimed is:

1. A DNA probe composition useful for detecting the presence of *Corynebacterium kutscheri* which is prepared by the process comprising of:
    digesting *C. kutscheri* DNA with restriction enzyme EcoR1 and resolving generated fragments according to their respective molecular weights,
    isolating EcoR1 digestion fragments capable of hybridizing with *C. kutscheri* DNA but incapable of hybridizing with nonpathogenic Corynebacterium DNA,
    cloning said isolated fragments into a plasmid capable of transforming bacteria,
    transforming bacteria with said plasmid containing the isolated fragments of *C. kutscheri* DNA,
    digesting said plasmids isolated from the resulting transformants with restriction enzyme HindIII and resolving and isolating generated fragments according to their respective molecular weights,
    identifying by hybridization the HindIII digestion fragments of cloned *C. kutscheri* DNA which are incapable of cross-reacting with nonpathogenic strains of Corynebacterium and incapable of cross-reacting with rat liver DNA, and
    labeling at least one of the isolated HindIII digestion fragments to obtain a DNA probe.

2. A DNA probe composition according to claim 1, wherein the DNA probe is at least one of three fragments which are about 1.6 kb, 1.7 kb, and 1.8 kb in size.

3. A DNA probe composition according to claim 2, wherein the transformed bacteria is *E. coli*.

4. A DNA probe composition according to claim 3, wherein the transformed bacteria is *E. coli* RR1.

5. A DNA probe composition according to claim 4, wherein the transformed bacteria is *E. coli* HB101 having the deposit accession number ATCC 53153.

6. A DNA probe composition according to claim 4, wherein the transformed bacteria is *E. coli* HB101 having the deposit accession number ATCC 53151.

7. A DNA probe composition according to claim 4, wherein the transformed bacteria is *E. coli* HB101 having the deposit accession number ATCC 53152.

* * * * *